United States Patent
Asukai et al.

(10) Patent No.: US 10,518,161 B2
(45) Date of Patent: Dec. 31, 2019

(54) SOUND-OUTPUT-CONTROL DEVICE, SOUND-OUTPUT-CONTROL METHOD, AND SOUND-OUTPUT-CONTROL PROGRAM

(71) Applicant: Sony Corporation, Tokyo (JP)

(72) Inventors: Masamichi Asukai, Kanagawa (JP); Katsuya Shirai, Kanagawa (JP); Makoto Inoue, Tokyo (JP); Akane Sano, Tokyo (JP)

(73) Assignee: Sony Corporation, Tokyo (JP)

( * ) Notice: Subject to any disclaimer, the term of this patent is extended or adjusted under 35 U.S.C. 154(b) by 66 days.

(21) Appl. No.: 14/473,087

(22) Filed: Aug. 29, 2014

(65) Prior Publication Data

US 2014/0369522 A1 Dec. 18, 2014

Related U.S. Application Data

(63) Continuation of application No. 11/519,033, filed on Sep. 11, 2006, now Pat. No. 8,858,453.

(30) Foreign Application Priority Data

Sep. 12, 2005 (JP) .................................. 2005-263328

(51) Int. Cl.
*A61B 5/02* (2006.01)
*A63B 71/06* (2006.01)
(Continued)

(52) U.S. Cl.
CPC ...... *A63B 71/0622* (2013.01); *A63B 24/0021* (2013.01); *A63B 71/0686* (2013.01);
(Continued)

(58) Field of Classification Search
CPC .................. A61B 5/02; A63B 71/0622; A63B 2071/0625

See application file for complete search history.

(56) References Cited

U.S. PATENT DOCUMENTS 5,527,239 A * 6/1996 Abbondanza .......... A63B 22/02
                                                                482/1
6,104,947 A 8/2000 Heikkila et al.
(Continued)

FOREIGN PATENT DOCUMENTS

JP 09-509877 T 10/1997
JP 10-155772 A 6/1998
(Continued)

OTHER PUBLICATIONS

Conconi et al., "Determination of the anaerobic threshold by a non-invasive field test in runners," 1982 Journal of Applied Physiology 52 (4): 869-873.

(Continued)

*Primary Examiner* — Christian Jang
(74) *Attorney, Agent, or Firm* — Wolf, Greenfield & Sacks, P.C.

(57) ABSTRACT

A sound-output-control device including an acquisition unit which acquires an anaerobic threshold, a reception unit which receives an input about exercise intensity, a calculation unit which calculates a value indicating a target heart rate of a user on the basis of the acquired anaerobic threshold and the received exercise-intensity input, a detection unit which detects a value indicating the current tempo of a physical exercise done by the user, and a control unit that controls a sound output on the basis of a result of a comparison of the target heart-rate value calculated by the calculation unit and the current physical-exercise-tempo value detected by the detection unit, so as to lead a heart rate of the user so that the heart rate of the user attains the target heart rate is provided.

32 Claims, 9 Drawing Sheets

(51) Int. Cl.
*G06F 19/00* (2018.01)
*A63B 24/00* (2006.01)
*H03G 3/20* (2006.01)
*A63B 22/00* (2006.01)

(52) U.S. Cl.
CPC ........... *G06F 19/3481* (2013.01); *H03G 3/20* (2013.01); *A63B 22/00* (2013.01); *A63B 24/0075* (2013.01); *A63B 2024/0025* (2013.01); *A63B 2071/0625* (2013.01); *A63B 2220/30* (2013.01); *A63B 2220/34* (2013.01); *A63B 2225/50* (2013.01); *A63B 2230/06* (2013.01); *A63B 2230/40* (2013.01)

(56) References Cited

U.S. PATENT DOCUMENTS

| | | | | |
|---|---|---|---|---|
| 6,132,337 | A * | 10/2000 | Krupka et al. | 482/8 |
| 6,176,241 | B1 | 1/2001 | Blau et al. | |
| 6,572,511 | B1 | 6/2003 | Volpe | |
| 6,662,032 | B1 * | 12/2003 | Gavish | A61B 5/0205 |
| | | | | 600/300 |
| 7,648,463 | B1 * | 1/2010 | Elhag | A61B 5/0205 |
| | | | | 351/41 |
| 2002/0109600 | A1 * | 8/2002 | Mault | A61B 5/1112 |
| | | | | 340/573.1 |
| 2004/0077934 | A1 | 4/2004 | Massad | |
| 2004/0116837 | A1 * | 6/2004 | Yamaguchi | A61B 5/02438 |
| | | | | 600/595 |
| 2005/0124463 | A1 * | 6/2005 | Yeo | A61B 5/02427 |
| | | | | 482/8 |
| 2005/0129253 | A1 | 6/2005 | Chen | |
| 2005/0219055 | A1 | 10/2005 | Takai et al. | |
| 2006/0111621 | A1 | 5/2006 | Coppi et al. | |
| 2007/0044641 | A1 * | 3/2007 | McKinney | A63B 71/0686 |
| | | | | 84/612 |
| 2007/0060446 | A1 | 3/2007 | Asukai et al. | |

FOREIGN PATENT DOCUMENTS

| | | |
|---|---|---|
| JP | 2001-198114 A | 7/2001 |
| JP | 2001-299980 A | 10/2001 |
| JP | 2001-346906 A | 12/2001 |
| JP | 2002-148369 A | 5/2002 |
| JP | 2002-148375 A | 5/2002 |
| JP | 2002-153430 A | 5/2002 |
| JP | 2002-301050 A | 10/2002 |
| JP | 2003-108154 A | 4/2003 |
| JP | 2003-177749 | 6/2003 |
| JP | 2003-177750 A | 6/2003 |
| JP | 2003-305146 | 10/2003 |
| JP | 3582211 | 10/2004 |
| JP | 2005-87731 | 4/2005 |
| JP | 2005-156641 A | 6/2005 |
| WO | WO 99/43392 A1 | 9/1999 |
| WO | WO 2005/082472 A1 | 9/2005 |

OTHER PUBLICATIONS

U.S. Appl. No. 11/519,033, filed Sep. 11, 2006, Asukai et al.

* cited by examiner

USAGE MODE

FIG. 12
MUSIC DATA LIST
| ID | ARTIST NAME | TRACK NAME | ALBUM NAME | TEMPO |
|---|---|---|---|---|
| 111 | X | A3 | A | 140 |
| 23 | Y | B4 | B | 132 |
| 109 | X | A1 | A | 124 |
| 7 | Z | D3 | D | 123 |
| 10 | Z | D6 | D | 120 |
| 46 | Y | C2 | C | 117 |
FIG. 13
RHYTHM GENERATION METHOD
| | |
|---|---|
| <RHYTHM 1> CHANNEL: 10<br>NOTE NUMBER: 64 (LOW CONGA) |  |
| <RHYTHM 2> CHANNEL: 10<br>NOTE NUMBER: 63 (OPEN HIGH CONGA) |  |
| <RHYTHM 3> CHANNEL: 10<br>NOTE NUMBER:69 (CABASA) |  |

SOUND-OUTPUT-CONTROL DEVICE, SOUND-OUTPUT-CONTROL METHOD, AND SOUND-OUTPUT-CONTROL PROGRAM

CROSS REFERENCES TO RELATED APPLICATIONS

This application is a continuation of and claims the benefit under 35 U.S.C. §120 of U.S. patent application Ser. No. 11/519,033, titled "SOUND-OUTPUT-CONTROL DEVICE, SOUND-OUTPUT-CONTROL METHOD, AND SOUND-OUTPUT-CONTROL PROGRAM" and filed on Sep. 11, 2006, which claims the benefit under 35 U.S.C. §119 of Japanese Patent Application 2005-263328, filed on Sep. 12, 2005, each of which is hereby incorporated by reference herein in its entirety.

BACKGROUND OF THE INVENTION

1. Field of the Invention

The present invention relates to a device such as a mobile-acoustic-reproduction device including a "Mini Disc (MD) (Registered Trademark of Sony Corporation)" player, a hard-disk player, a memory player, and so forth, a method used for the device, and a program.

2. Description of the Related Art

For increasing health and taking a precautionary measure against adult diseases, physical exercises including running, jogging, walking, cycling, and so forth are widely and commonly performed at appropriate intensity, as aerobic exercises, which are highly effective at burning fat. Further, there have been provided various devices and/or apparatuses which support a user doing an exercise by notifying the user of information about a result of the exercise. The above-described devices and/or apparatuses are widely used.

Hitherto, when performing an exercise such as running, jogging, walking, etc., pedometers which count the number of steps have been widely used, so as to know the amount of exercises done by the user. Further, in recent years, multifunctional wrist-watch-type heart-rate meters have been provided. The multifunctional wrist-watch-type heart-rate meter allows for measuring the heart rate of a user doing an exercise, calculating various values of excess post-exercise oxygen consumption (EPOC), a respiration rate, a ventilation quantity, an oxygen intake, an energy-consumption amount, and so forth on the basis of the measured heart rate, and showing the calculated various values to the user. Here, the above-described EPOC value indicating the training intensity has come to attention of late mainly in Europe. The EPOC value is calculated, so as to measure a load placed on the user's body on the basis of an oxygen amount necessary to bring the user's body back to the resting state after the user finishes training. Therefore, the above-described oxygen amount may be referred to as an excessive oxygen amount.

Further, watch-type devices which can measure the running (walking) distance, perform calorie calculation, and provide sound, so as to control the pace of an exercise, so-called pitch meters which provide sound and/or light, so as to control the exercise pace, mobile phone terminals which have the pitch-meter function, so as to calculate the number of steps, a distance, and a calorie consumption, have been provided and widely used, for example.

Further, Japanese Unexamined Patent Application Publication No. 2003-305146 discloses an invention about an exercise-support system that motivates a user to start walking and that supports the user so that the user can enjoy exercising without interruption. More specifically, the exercise-support system includes a user terminal and a center device that are connected to each other via a communication network. The amount of an exercise done by the user to music output (reproduced) by the user terminal is calculated on the basis of personal-profile information or the like stored in the center device and the user is provided with the calculated exercise amount.

Thus, each of various devices and/or apparatuses provided in the past, so as to support users doing exercises, can measure information about a result of an exercise done by the user with relative precision and notify the user of the result information, where the result information indicates how much exercises the user had done, how much calories the user had consumed, and so forth. Therefore, the above-described devices and/or apparatuses are now widely used so that the user who does an exercise and/or wants to continue doing the exercise is provided with an index and/or a guideline.

SUMMARY OF THE INVENTION

However, each of the above-described pedometer, heart-rate meter, pitch meter, exercise-support system only provides the user with feedback on information about a result of the exercise done by the user. Namely, the above-described pedometer, heart-rate meter, pitch meter, exercise-support system have no function necessary to do a so-called fitness exercise, which makes it difficult for them to lead the exercise done by the user, so as to burn fat through an aerobic exercise.

In that case, the user has to determine whether or not the user had done a target exercise to a sufficient degree by studying information provided through the above-described devices and/or apparatuses. Therefore, if the user is not strong-willed, it is difficult for the user to attain a target exercise amount, or the user may do exercises more than necessary. Thus, it is difficult for the user to do exercises appropriately without interruption.

Accordingly, the present invention allows for doing an aerobic exercise at target intensity with efficiency, no stress, and stability.

Therefore, a sound-output-control device according to an embodiment of the present invention includes an acquisition unit which acquires the anaerobic threshold of a user, a reception unit which receives an input about exercise intensity, a calculation unit which calculates a value indicating a target heart rate of a user on the basis of the acquired anaerobic threshold and the received exercise-intensity input, a detection unit which detects a value indicating the current tempo of a physical exercise done by the user, and a control unit that controls a sound output on the basis of a result of a comparison of the target heart-rate value calculated by the calculation unit and the current physical-exercise-tempo value detected by the detection unit, so as to lead a heart rate of the user so that the heart rate of the user attains the target heart rate.

According to the above-described sound-output-control device, the acquisition unit acquires an anaerobic threshold (AT) of a user who is going to do a physical exercise. More specifically, the acquisition unit acquires a predetermined AT, an AT input by the user, or an AT obtained by measuring the heart rate of the user and analyzing the measured heart rate. Further, the reception unit receives an input about the exercise intensity desired by the user who is going to do the physical exercise.

Further, the AT acquired by the acquisition unit denotes a switch point (a change point) where the physical exercise done by the user is changed from an aerobic exercise to an anaerobic exercise. The AT can be represented as the heart rate, a respiratory quotient denoting the ratio between the amount of oxygen taken through breathing during the physical exercise and the amount of discharged carbon dioxide, the value of lactic acid, and so forth of the user doing the physical exercise.

Thus, the calculation unit calculates a value indicating a target heart rate desired by the user doing the physical exercise by using the acquired AT and the received exercise intensity. Further, the detection unit detects a value indicating the current tempo of the physical exercise done by the user.

Then, as has been described, the control unit controls an output of sound presented to the user, so as to lead the physical exercise done by the user so that the heart rate of the user doing the physical exercise becomes the target heart rate, on the basis of the calculated target heart-rate value and the detected physical-exercise-tempo value. The sound presented to the user includes various types of sound such as music, rhythm sound, a human voice, etc.

The above-described output control is performed, so as to control various processing procedures performed for sound to be output. For example, the output control includes selection of music or the like to be output (sound selection), control of the tempo of sound such as the music to be output, control of generation and/or synthesis of sound such as music played at a target tempo, control of a time period during which the sound such as the music to be output is output, and so forth. Namely, in this specification, the sound-output processing includes various processing procedures performed, so as to read a sound signal from a recording medium and generate an analog speech signal transmitted to a speaker or the like on the basis of the read sound signal.

Further, the user does an exercise including walking, jogging, running, cycling, and so forth to the output sound such as music. Subsequently, the user doing the exercise can do an aerobic exercise at target intensity with efficiency, no stress, and stability. Further, the user can do the aerobic exercise effectively.

Thus, the present invention allows for leading a user so that the user can do a physical exercise including running, jogging, walking, cycling, and so forth with efficiency, no stress, and stability, as an aerobic exercise. Subsequently, the user can do the aerobic exercise effectively.

BRIEF DESCRIPTION OF THE DRAWINGS

FIG. 5 shows another example method of estimating the AT;

FIG. 12 shows an example musical-data list; and

FIG. 13 specifically shows an example method of automatically generating music played at a target tempo.

DESCRIPTION OF THE PREFERRED EMBODIMENTS

Hereinafter, a device, a method, and a program according to an embodiment of the present invention will be described with reference to the attached drawings. In the embodiment described below, the above-described device, method, and program are used for a mobile-music-reproduction device (a sound-output-control device) including a mobile memory player, a mobile hard-disk player, a mobile "Mini Disc (MD) (Registered Trademark of Sony Corporation)" player, and so forth.

[Example Mode of Usage of Mobile-Music-Reproduction Device]

Figure 1:
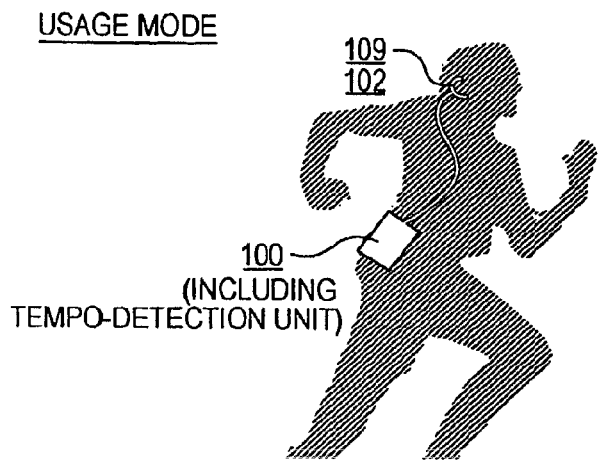
FIG. 1 shows a mode of usage of a reproduction device 100 according to an embodiment of the present invention.

FIG. 1 shows an example mode of usage of a mobile-music-reproduction device (hereinafter simply referred to as a reproduction device) 100 according to an embodiment of the present invention. As shown in FIG. 1, the reproduction device 100 is mounted on the body of a user at a predetermined position such as hips of the user doing a physical exercise including walking, jogging, running, cycling, and so forth.

The music or the like corresponding to a sound signal processed in the reproduction device 100 is output via headphones 100 connected to the reproduction device 100 and presented to the user. Subsequently, the user can perform a target physical exercise including walking, jogging, running, cycling, and so forth while listening to the music and using the music, as a pacemaker.

Then, the reproduction device 100 of the above-described embodiment includes a tempo-detection unit having an acceleration sensor in its main body, so as to detect the body motion (e.g., a vertical motion of the body) of the user doing the physical exercise. Subsequently, it becomes possible to measure the physical-exercise rhythm and detect the physical-exercise tempo indicating the cycle of the physical-exercise rhythm.

Further, a heart-rate sensor is attached to the headphones 109, as a heart-rate detection unit. The heart-rate sensor is mounted onto an earlobe of the user, for example, so that the heart rate of the user is detected. The heart-rate sensor can also detect the user's heart rate changing according to the physical exercise (the heart rate per unit time).

Further, as will be described later, the reproduction device 100 of the above-described embodiment measures the user's heart rate when the user does the physical exercise while changing an exercise load gradually, or in stages. Further, the reproduction device 100 analyzes the measurement result according to a predetermined method so that the anaerobic threshold (AT) of the user is obtained. As described above, the AT denotes a switch point (a change point) where the physical exercise done by the user is changed from an aerobic exercise to an anaerobic exercise.

Then, the reproduction device 100 of the above-described embodiment obtains the AT on the basis of the heart rate of the user doing the exercise, as described above, and obtains a value indicating a target physical state on the basis of the obtained AT and exercise-intensity information input by the user. In the above-described embodiment, the heart rate is obtained, as the target-physical-state value. Then, the reproduction device 100 controls an output (reproduction) of sound such as music presented to the user by using information about the tempo of the physical exercise done by the user, so as to lead the tempo of the like of the physical exercise done by the user so that a target heart rate is attained. Subsequently, it becomes possible for the user to perform an aerobic exercise with stability, effect, and no undue stress.

[Example Configuration of Mobile-Sound-Reproduction Device]

Figure 2:
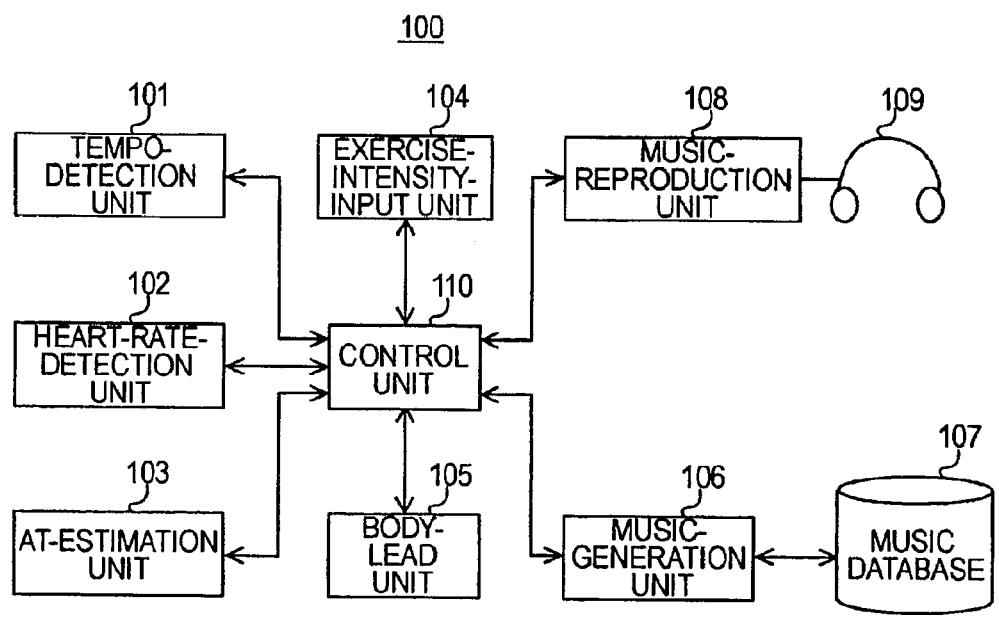
FIG. 2 is a block diagram illustrating an example configuration of the reproduction device 100.

FIG. 2 is a block diagram illustrating an example configuration of the reproduction device 100 of the above-described embodiment. As shown in FIG. 2, the reproduction device 100 includes a tempo-detection unit 101, a heart-rate detection unit 102, an AT-estimation unit 103, a physical-intensity-input unit 104, a body-lead unit 105, a music-generation unit 106, a music database 107, a music-reproduction unit 108, the headphones 109, and a control unit 110.

The control unit 110 is a microcomputer including, though not shown, a central processing unit (CPU), a read only memory (ROM), a random access memory (RAM), a nonvolatile memory, a clock circuit, and so forth that are connected to one another via a CPU bus. The control unit 110 controls each of the above-described parts of the reproduction device 100.

Though not shown, the CPU of the control unit 110 executes a program, so as to generate control signals transmitted to the parts of the reproduction device 100. Thus, the CPU executes main part of controlling the reproduction device 100. Further, the ROM stores a program executed by the CPU and/or various data items necessary for performing processing. The RAM is mainly used, as a work area. Further, data stored in the nonvolatile memory is not deleted even though the power is shut down. Further, data stored in the nonvolatile memory can be rewritten. For example, various setting parameters are stored in the nonvolatile memory. The clock circuit presents information about the current time.

As described above, the tempo-detection unit 101 includes the acceleration sensor and measures the physical-exercise rhythm (a continuous motion of the user's body) on the basis of a vertical motion or the like of the user's body. Further, the tempo-detection unit 101 obtains the physical-exercise tempo (the speed of the physical-exercise rhythm) indicating the cycle of the physical-exercise rhythm on the basis of the measurement result and notifies the control unit 110 of the obtained physical-exercise tempo. That is to say, the tempo-detection unit 101 detects the vertical motions of the user's body, that is, the physical exercises done by the user at regular intervals. Subsequently, the tempo-detection unit 101 recognizes the rhythm of the physical exercise done by the user, obtains information about the physical-exercise tempo indicating the cycle of the physical-exercise rhythm, and notifies the control unit 110 of the physical-exercise-tempo information.

In the above-described embodiment, the physical-exercise rhythm is measured on the basis of the vertical motion of the user's body. However, the present invention can be achieved without being limited to the above-described embodiment. For example, if the value of a lateral motion of the user's body is larger than that of a vertical motion of the user's body, as is the case where the user does cycling, the physical-exercise rhythm may be measured on the basis of the lateral motion.

The heart-rate detection unit 102 includes a heart-rate sensor supporting a photoelectric-pulse-wave-detection method, for example, so as to measure the heart rate of the user via the earlobe of the user doing a physical exercise, and inform the control unit 110 of the measured heart rate. Information about the heart rate detected by the heart-rate detection unit 102 is used, as a value indicating the current physical state of the user, transmitted to the AT-estimation unit 103 (described later) via the control unit 110, and used, so as to estimate the AT of the user.

Then, the AT-estimation unit 103 estimates the AT on the basis of a change in the user's heart rate obtained where the body leading is performed by using music played at a different tempo. Methods of estimating the AT will be described later. According to one of the AT-estimation methods, the body leading is performed so that an exercise load placed on the user doing a physical exercise is increased gradually. Therefore, music is output (reproduced) so that the tempo thereof is quickened gradually. The user performs a predetermined exercise to the output music. At that time, the user's heart rate is measured via the heart-rate-detection unit 102 and the AT is estimated on the basis of the measured heart rate.

It is noted that the AT is not fluctuated significantly at frequent intervals. Therefore, the AT may be estimated, for example, once a year, once a half year, once several months, and so forth, and stored and held in the nonvolatile memory or the like of the control unit 110. Subsequently, the stored and held AT can be used when the user does an ordinary training.

Therefore, the reproduction device 100 operates in three modes relating to the sound output (reproduction), where three modes include an AT-estimation mode, a training mode, and a usual-reproduction mode. In the AT-estimation mode, as described above, predetermined music is output while changing the tempo thereof gradually, the user's heart rate is measured while the physical exercise done by the user is led, and the AT is estimated on the basis of the measured heart rate.

Further, in the training mode which will be described later in detail, a value indicating a target physical state, more specifically, a target heart rate is obtained on the basis of the stored and held AT and information about the exercise intensity, the exercise-intensity information being input by the user via the exercise-intensity-input unit 104 which will be described later. Then, the user's physical exercise is led, the tempo or the like of output sound is controlled, and the sound is output (reproduced) so that the physical state of the user attains the target heart rate. Further, in the usual-reproduction mode, sound is output (reproduced) at a predetermined tempo, as usual, without controlling the tempo of the output sound, for example, and the output sound is presented to the user.

Further, as described above, the AT is stored and held in the nonvolatile memory or the like of the control unit 110. Therefore, an AT input by the user can be stored and held in the nonvolatile memory or the like of the control unit 110 for use. For example, in a sport gym and/or a research institute such as a university, the AT can be measured in precision by using sophisticated equipment and/or a sophisticated apparatus. Therefore, the AT measured in the sport gym and/or the research institute can be input via a user-operation unit such as the exercise-intensity input unit 104 which will be described later, and stored and held in the nonvolatile memory or the like for use.

As described above, the exercise-intensity input unit 104 receives information indicating the exercise intensity, the information being input by the user, changes the exercise-intensity information into an electric signal, and transmits the electric signal to the control unit 110. The exercise-intensity information indicates the intensity of a physical exercise that will be performed by the user. The exercise-intensity information is shown, as "light", "ordinary", and "heavy", for example. The exercise-intensity input unit 104 has operation keys including numeric keys, a reproduction key, a stop key, a pause key, a fast-forward key, a fast-reverse key, and so forth, and various function keys, receives information other than the exercise-intensity information and/or an instruction input by the user, changes the information and/or the instruction into an electric signal, and transmits the electric signal to the control unit 110.

The body-guide unit 105 calculates a value indicating a target physical state on the basis of the AT obtained through the AT-estimation unit 113 and the exercise-intensity information obtained through the exercise-intensity input unit 104. In the above-described embodiment, the body-guide unit 105 calculates the target heart rate, as the target physical state. Then, the body-guide unit 105 calculates a target tempo on the basis of the target heart rate, the heart rate obtained through the heart-rate detection unit 102, and the tempo information relating to the physical exercise done by the user, the tempo information being obtained by the tempo-detection unit 101.

The music-generation unit 106 generates music played at the target tempo calculated by the body-guide unit 105 by using music contents stored and held in the music database 107 under the control of the control unit 110. The music-reproduction unit 108 generates an analog-sound signal transmitted to the headphones 109 on the basis of music data generated in the music-generation unit 106, and transmits the analog-sound signal to the headphones 109. Subsequently, music played at the controlled tempo is output from the headphones 109. Therefore, the user can perform a target aerobic exercise at target exercise intensity by performing a physical exercise to the output music.

Further, the music-generation unit 106 not only controls the tempo of output music, but also performs various processing procedures performed for sound to be output, as described above. Namely, the various processing procedures include selecting a track by searching music data (track contents) stored in the music database 107 for data on music played at the target tempo, generating and/or synthesizing music or the like played at the target tempo and/or a target rhythm, controlling a time period during sounds are output (reproduced), and so forth.

In the music-reproduction unit 108, the sound volume and/or the sound quality can be adjusted under the control of the control unit 110, where the control is performed according to an instruction that is input by the user and that is transmitted via the exercise-intensity input unit 104. Further, the music database 107 is provided, as a recording medium including a magneto-optical disk such as an "Mini Disc (MD) (Registered Trademark of Sony Corporation)", an optical disk, an integrated-circuit (IC) memory card, a small hard disk, and so forth, where many data items including musical data and meta data relating to music, data on musical materials, and so forth are accumulated onto the recording medium. The music database 107 will be described later in detail.

Further, though not shown, the reproduction device 100 of the above-described embodiment includes an external input-and-output interface. Therefore, upon receiving music data and/or the musical-material data transmitted from an external apparatus such as a personal computer (PC), the reproduction device 100 can store and hold the above-described data in the music database 107, for example.

Further, when the recording medium including the music database 107 is provided, as a removable recording medium, that is to say, when the recording medium can be mounted on and removed from the main body of the reproduction device 100 of the above-described embodiment, it becomes possible to use a different music database by replacing the above-described recording medium with another recording medium.

[Details on Processing (Operations) Performed by Reproduction Device 100]

Next, each of tempo-detection processing, AT-estimation processing, physical-exercise-guide processing that are performed by the reproduction device 100 of the above-described embodiment will be described.

[Details on Tempo-Detection Processing]

The tempo-detection processing is achieved mainly by functions of the tempo-detection unit 101. As described above, the tempo-detection unit 101 detects the physical-exercise tempo indicating the rhythm cycle of a physical exercise performed by the user. In the AT-estimation mode, as will be described later, the physical-exercise tempo is used, as a determination reference, so as to determine whether or not the user performs the physical exercise according to a sound signal such as music presented by the above-described reproduction device 100. In the training mode, the physical-exercise tempo is used, as a single item of data used for leading the physical exercise done by the user in an appropriate manner without placing an unnecessary load on the user.

The tempo-detection unit 101 of the reproduction device 100 measures the rhythm of the physical exercise done by the user through the acceleration sensor provided in the tempo-detection unit 101 and calculates autocorrelation of the measurement result. Subsequently, the tempo of the physical exercise is detected. Hereinafter, processing performed by the tempo-detection unit 101 will be described in detail with reference to FIGS. 3A and 3B.

Figure 3A:
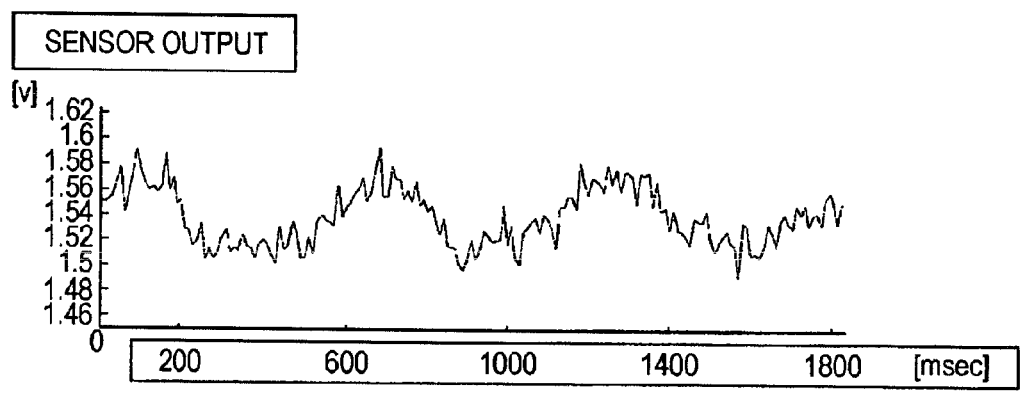
FIG. 3A illustrates user-tempo detection performed by a tempo-detection unit.

FIG. 3A shows an example waveform output from the acceleration sensor of the tempo-detection unit 101. The waveform shown in FIG. 3A is output from the acceleration sensor while the user wearing the reproduction device 100 of the above-described embodiment around his/her hips performs jogging, for example. Therefore, the waveform is generated according to the rhythm of the physical exercise done by the user. As shown in FIG. 3A, the waveforms output from the acceleration sensor fluctuate mincingly.

The above-described fluctuation is caused by a small vibration of the user's body, where the small vibration occurs when a leg of the user doing jogging leaves the ground, or when the leg that had left the ground touches the ground, for example. Otherwise, the above-described fluctuation is caused when various noises are added to vertical motion of the user's body due to a vibration of the reproduction device 100, the vibration being caused by movements of the user, for example.

According to the above-described embodiment, therefore, the tempo-detection unit 101 calculates autocorrelation of the detection result output from the acceleration sensor, thereby removing a waveform component having no correlation to the time direction and extracting only a waveform component correlated to the time direction. Subsequently, the tempo-detection unit 101 correctly acquires information about the rhythm of physical exercises performed by the user at regular time intervals and correctly detects the tempo of the physical exercises performed by the user.

Figure 3B:
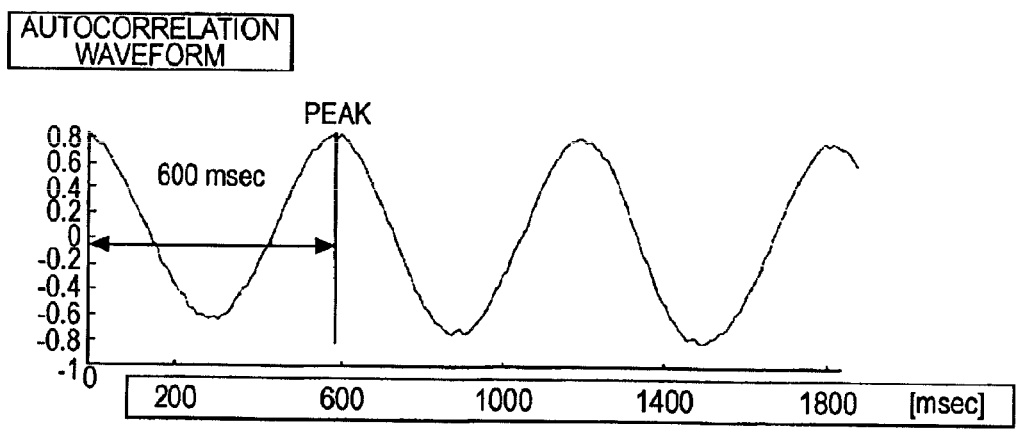
FIG. 3B also illustrates the user-tempo detection performed by the tempo-detection unit.

FIG. 3B shows autocorrelation waveforms of the waveforms shown in FIG. 3A, the waveforms being output from the acceleration sensor. When the waveform component having no correlation to the time direction is removed and only the waveform component correlated to the time direction is extracted by calculating the autocorrelation, the waveforms (autocorrelation waveforms) corresponding to the rhythm of physical exercises done by the user at regular time intervals can be obtained, as shown in FIG. 3B.

Then, information about the time corresponding to a single cycle of the autocorrelation waveforms shown in FIG. 3B can be acquired, as an actual tempo of physical exercise done by the user. In the case where the waveforms shown in FIGS. 3A and 3B are obtained, the time period corresponding to the single cycle is six hundred milliseconds. Therefore, it is detected that the single cycle of the tempo of the physical exercise done by the user is six hundred milliseconds. Information about the detected cycle is transmitted to the control unit 110, so as to be used for performing various processing procedures.

[Details on AT-Estimation Processing]

Next, anaerobic-threshold (AT) estimation processing will be described. The AT estimation processing is achieved mainly by the AT-estimation unit 103 and the control unit 110 that operate in concert with each other. In the AT-estimation mode, the AT-estimation unit 103 of the reproduction device 100 of the above-described embodiment estimates the AT on the basis of the heart-rate information transmitted from the heart-rate detection unit 102 via the control unit 110. The AT can be estimated according to various methods. Namely, the AT can be estimated according to method (1) performed by using a respiratory quotient, method (2) performed by using a lactic-acid value, method (3) performed by using a heart rate, and so forth. In the above-described embodiment, method (3) is used so that the AT can be estimated with relative ease.

The AT of pulsation is referred to as a heart-rate threshold (HRT). The HRT is calculated by performing methods (a) and (b). According to method (a), the heart rate corresponding to an inflection point where the heart-rate change caused by an increased exercise load becomes nonlinear is obtained. The above-described method is referred to as Conconi test. According to method (b), an unstable heart rate caused by an increased exercise load is obtained. The general outline of each of methods (a) and (b) will be described.

Figure 4:
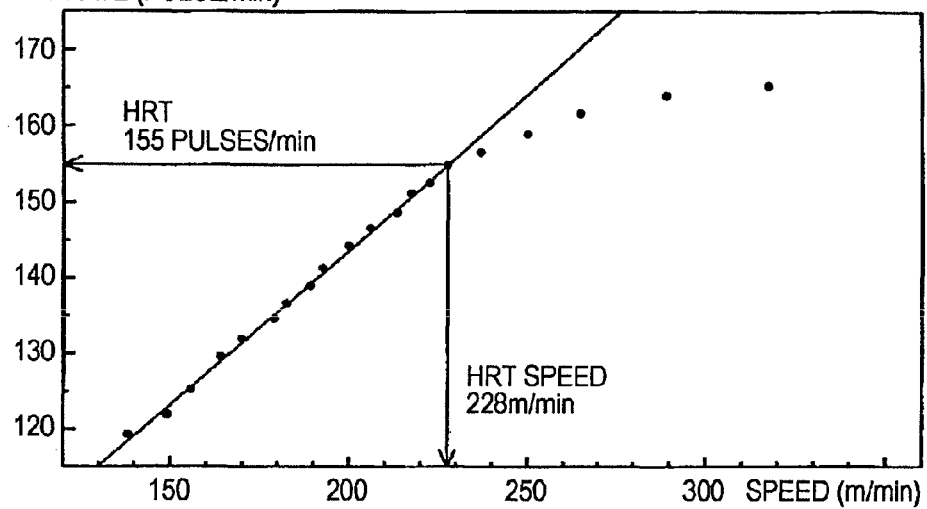
FIG. 4 shows an example method of estimating an anaerobic threshold (AT)

FIG. 4 illustrates method (a) performed, so as to calculate the heart rate corresponding to the inflection point where the heart-rate change caused by the increased exercise load becomes nonlinear, as the AT. In FIG. 4, the lateral axis shows the exercise speed corresponding to an exercise load placed on the user doing a physical exercise, and the vertical axis shows the heart rate of the user doing the physical exercise.

Namely, FIG. 4 shows a graph illustrating the heart-rate change of the user jogging with gradually increasing speed. If the user starts jogging at a speed of 130 meters per minute and increases the speed step by step every predetermined time period, for example, the user's heart rate increases linearly until a speed on the order of 228 meters per minute is attained. However, when the jobbing speed exceeds the speed on the order of 228 meters per minute, the change in the user's heart rate generates a non-linear form in place of a linear form.

Thus, the heart rate corresponding to the inflection point (flection point) where the change in the user's heart rate generates the non-linear form can be used, as the AT. In an example shown in FIG. 4, the AT which is shown, as the HRT, corresponds to 155 pulses/min (155 pulses per minute). Namely, 155 pulses/min can be used, as the AT.

Figure 5:
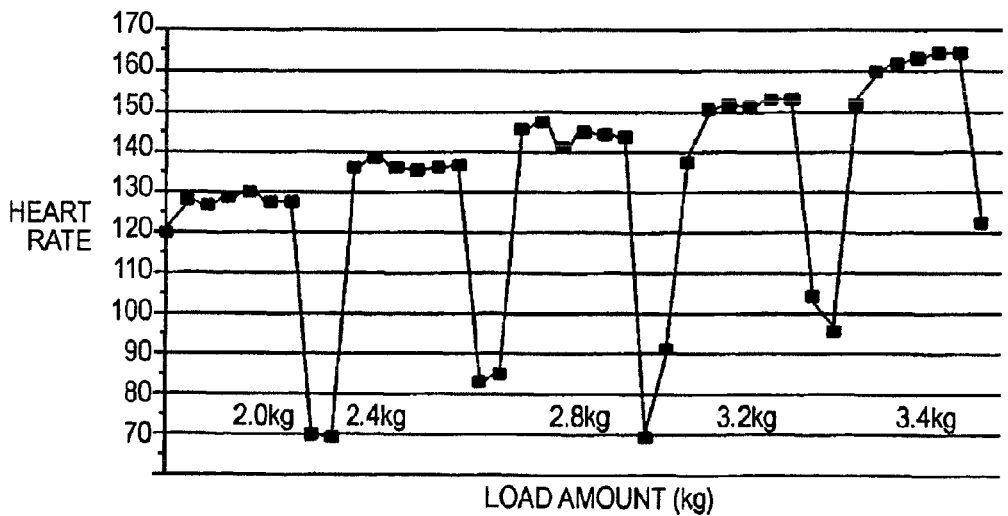

On the other hand, FIG. 5 illustrates method (b) performed, so as to calculate the unstable heart rate caused by the increased exercise load. In FIG. 5, the lateral axis shows the amount (weight) of a load placed on the user doing a physical exercise and the vertical axis shows the heart rate of the user doing the physical exercise.

FIG. 5 shows an example where the user performs the physical exercise by using a bicycle-type training machine. More specifically, FIG. 5 shows a graph illustrating a change in the user's heart rate where a load placed on a leg of the user pedaling the bicycle-type training machine is gradually increased every predetermined time period. In FIG. 5, the load placed on the user is 2.0 kg at first and increased step by step every predetermined period. Further, a predetermined interval is provided before increasing the load.

Further, as shown in FIG. 5, the user's heart rate becomes almost constant at a level on the order of 130 pulses/minute, where the exercise load is 2.0 kg. When the exercise load is 2.4 kg, the user's heart rate becomes almost constant at a level slightly lower than a level of 140 pulses/minute. When the exercise load is 2.8 kg, the user's heart rate becomes almost constant at a level near a level of 145 pulses/minute, even though there are insignificant variations in the heart rate. When the exercise load is 3.2 kg, the user's heart rate becomes constant at a level slightly higher than a level of 150 pulses/minute. However, when the exercise load is 3.4 kg, the user's heart rate increases and exceeds a level of 155 pulses/minute. Namely, when the exercise load becomes 3.4 kg, the heart rate becomes unstable. A heart rate obtained just moments before the unstable heart rate occurs is represented as 155 pulses/minute which should be calculated, as the AT.

Figure 6:
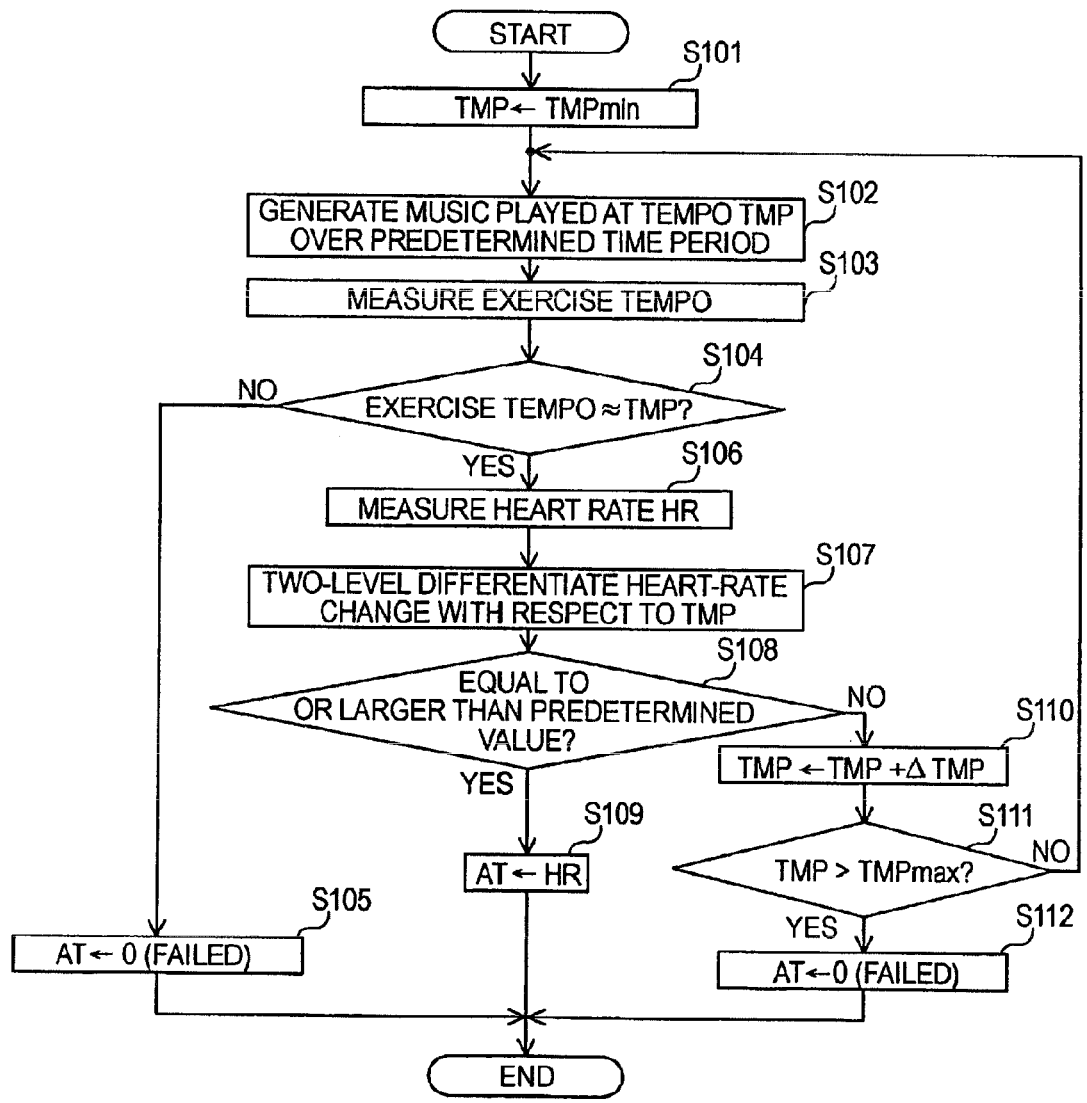
FIG. 6 is a flowchart illustrating the example AT-estimation method shown in FIG. 4.
Figure 7:
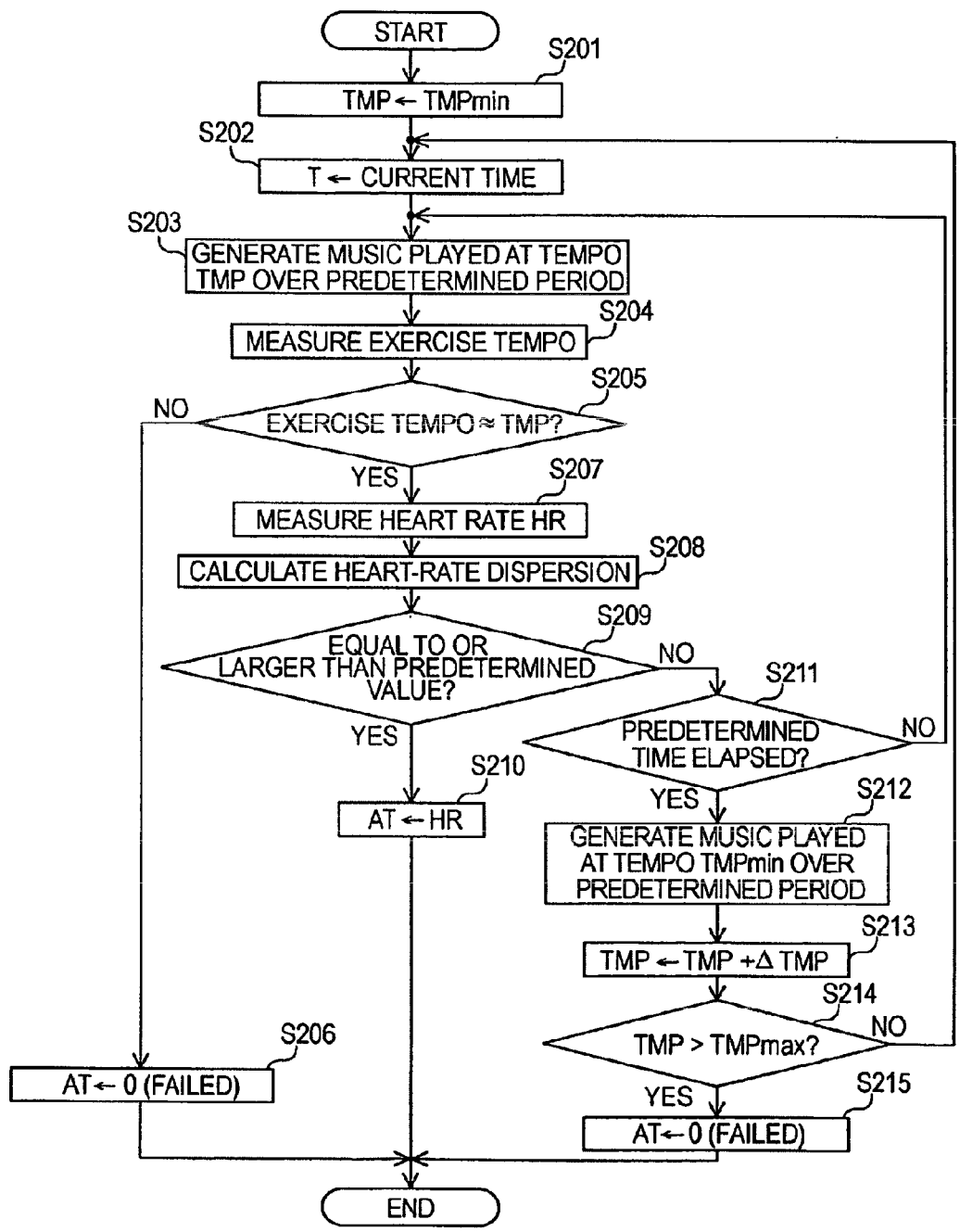
FIG. 7 is a flowchart illustrating the example AT-estimation method shown in FIG. 5.

Next, flowcharts shown in FIGS. 6 and 7 illustrate details on processing performed, so as to calculate the AT of the user by using the heart rate, as a value indicating the physical state of the user, as described above with reference to FIGS. 4 and 5.

First, method (a) will be specifically described. FIG. 6 is a flowchart illustrating the method of calculating the heart rate corresponding to the inflection point, as the AT. The processing shown in FIG. 6 is actually performed by the control unit 110 controlling the parts of the reproduction device 100.

As described above, when the reproduction device 100 of the above-described embodiment receives an instruction input by the user via the operation unit in the AT-estimation mode, the instruction being generated, so as to start the AT estimation, the control unit 110 controls the AT-estimation unit 103 and sets a predetermined minimum tempo value TMPmin to a variable TMP indicating the music tempo (step S101). Next, the control unit 110 generates and outputs (reproduces) music played at a tempo represented as the variable TMP over a predetermined time period by controlling the music-generation unit 106 and the music-reproduction unit 108 and provides the user with the music (step S102). The user performs an exercise to the tempo of the provided music.

Then, the control unit 110 controls the tempo-detection unit 101 and measures the current tempo of the physical exercise done by the user (step S103), and determines whether or not the measured physical-exercise tempo is substantially equal to the tempo TMP of the output music (step S104). The determination processing corresponding to step S104 is performed, so as to determine whether or not the user is doing the physical exercise at the tempo of the output music.

At step S104, if it is determined that the measured physical-exercise tempo is not substantially equal to the tempo TMP of the output music, namely, if it is determined that the user is not doing the physical exercise to the tempo of the output music, it is determined that it is difficult to estimate the AT appropriately. In that case, zero is assigned to the AT (step S105) and the processing shown in FIG. 6 is terminated.

At step S104, if it is determined that the measured physical-exercise tempo is substantially equal to the tempo TMP of the output music, namely, if it is determined that the user does the physical exercise to the tempo of the output music, the control unit 110 controls the heart-rate detection unit 102 so that the heart rate HR of the user is measured (step S106).

Then, the control unit 110 two-level differentiates the heart-rate change notified by the heart-rate detection unit 102 with respect to the tempo TMP (step S107) and determines whether or not a result of the two-level differentiation shows a value equal to or larger than a predetermined fixed value (step S108). The determination processing corresponding to step S108 is performed, so as to determine whether or not the load placed on the user is increased and the heart-rate change reaches an inflection point without showing the linear form. Namely, the determination processing corresponding to step S108 is performed, so as to determine whether or not the physical exercise done by the user is changed from an aerobic exercise to an anaerobic exercise.

At step S108, if it is determined that the value of a result of the two-level differentiation performed at step S107 is equal to or larger than the predetermined fixed value, the control unit 110 determines the current heart rate HR to be the AT (step S109), since the position of the current heart rate corresponds to the inflection point, and terminates the processing shown in FIG. 6.

At step S108, if it is determined that the value of the result of the two-level differentiation performed at step S107 is not equal to or larger than the predetermined fixed value, the control unit 110 determines that the current heart rate HR does not reach the AT and adds a fixed value ΔTMP to the tempo TMP by controlling the AT-estimation unit 103 (step S110). Further, the control unit 110 determines whether or not the value of tempo TMP is larger than a predetermined maximum value TMPmax of the tempo TMP (step S111).

At step S111, if the value of tempo TMP is larger than the predetermined maximum value TMPmax, it is determined that the calculation of the AT is failed, 0 (zero) is assigned to the AT (step S112) and the processing shown in FIG. 6 is terminated. Further, at step S111, if it is determined that the value of tempo TMP is not larger than the predetermined maximum value TMPmax, the processing corresponding to step S102 and afterward is performed again. Then, at step S110, music played at the tempo TMP changed by as much as ΔTMP is generated and output again, and the processing corresponding to steps subsequent to step S110 is performed again.

Thus, as has been described with reference to FIG. 4, the heart rate corresponding to the inflection point where the heart-rate change caused by the increased exercise load shows the non-linear form can be obtained, as the AT.

First, method (b) will be specifically described. FIG. 7 is a flowchart illustrating the method of calculating the heart rate corresponding to the unstable heart rate caused by the increased exercise load, as the AT. The processing shown in FIG. 7 is actually performed by the control unit 110 controlling the parts of the reproduction device 100.

As is the case with the processing described with reference to FIG. 6, when the reproduction device 100 of the above-described embodiment receives an instruction input by the user via the operation unit in the AT-estimation mode, the instruction being generated, so as to start the AT estimation, the control unit 110 controls the AT-estimation unit 103 and sets the predetermined minimum tempo value TMPmin to the variable TMP of the music tempo (step S201). Further, the control unit 110 acquires information about the current time from the clock circuit thereof and sets the current-time information to a time variable T (step S202).

Next, the control unit 110 generates music played at a tempo represented as the variable TMP over a predetermined time period, outputs the music, and provides the user with the music by controlling the music-generation unit 106 and the music-reproduction unit 108 (step S203). The user does an exercise to the tempo of the provided music. Then, the control unit 110 controls the tempo-detection unit 101 so that the current tempo of the physical exercise done by the user is measured (step S204), and determines whether or not the measured physical-exercise tempo is substantially equal to the tempo TMP of the output music (step S205). The determination processing corresponding to step S205 is performed, so as to determine whether or not the user is doing the physical exercise to the tempo of the output music.

At step S205, if it is determined that the measured physical-exercise tempo is not substantially equal to the tempo TMP of the output music, namely, if it is determined that the user is not doing the physical exercise to the tempo of the output music, it is determined that it is difficult to estimate the AT appropriately. In that case, 0 (zero) is assigned to the AT (step S206) and the processing shown in FIG. 7 is terminated.

At step S205, if it is determined that the measured physical-exercise tempo is substantially equal to the tempo TMP of the output music, namely, if it is determined that the user is doing the physical exercise at the tempo of the output music, the control unit 110 controls the heart-rate detection unit 102 so that the heart rate HR of the user is measured (step S207).

Then, the control unit 110 acquires information about the current time from the clock circuit, and calculates the dispersion in the heart rate that had been measured from the time shown by the time variable T to the current time by controlling the AT-estimation unit 103 (step S208). Further, the control unit 110 determines whether or not the values of the calculated heart-rate dispersion are equal to or larger than a predetermined fixed value (step S209). The determination processing corresponding to step S209 is performed, so as to determine whether or not the physical exercise is changed from the aerobic exercise to the anaerobic exercise, because the load placed on the user is increased and the heart-rate change (the dispersion) does not fall within a predetermined range.

At step S209, if it is determined that the values of the heart-rate dispersion are equal to or larger than the predetermined fixed value, the control unit 110 determines that the physical exercise is changed from the aerobic exercise to the anaerobic exercise and determines the heart rate HR obtained at that time to be the AT (step S210). Then, the control unit 110 terminates the processing shown in FIG. 7.

At step S209, if it is determined that the values of the heart-rate dispersion are not equal to or larger than the predetermined fixed value, the control unit 110 acquires information about the current time, compares the acquired current-time information and the time variable T, and determines whether or not a predetermined time period elapsed (step S211). The processing corresponding to step S211 is performed, so as to measure the predetermined time period where the user performs the physical exercise under a fixed exercise load.

At step S211, if it is determined that the predetermined time period did not elapse, the control unit 110 performs the processing corresponding to step S203 and afterward again, generates and outputs the music played at the tempo indicated by the variable TMP over a predetermined time period, and instructs the user to perform the physical exercise to the output music. At step S211, if it is determined that the predetermined time period elapsed, it is determined that the current heart rate HR does not attain the AT, and the control unit 110 generates and outputs music played at a tempo indicated by TMPmin over a predetermined time period by controlling the music-generation unit 106 and the music-reproduction unit 108 (step S212). The user does the physical exercise at the tempo of the output music.

The processing corresponding to step S212 is performed, so as to decrease the heart rate of the user temporarily so that the heart rate is stabilized before increasing the heart rate by increasing the exercise load. Namely, the processing corresponding to step S212 is performed, so as to provide an interval period.

Then, the control unit 110 adds the predetermined fixed value ΔTMP to the tempo TMP by controlling the AT-estimation unit 103 (step S213). Further, the control unit 110 determines whether or not the value of tempo TMP is larger than the predetermined maximum value TMPmax of the tempo TMP (step S214). At step S214, if the value of the tempo TMP is larger than the predetermined maximum value TMPmax, it is determined that the calculation of the AT is failed, 0 (zero) is assigned to the AT (step S215), and the processing shown in FIG. 7 is terminated.

Further, at step S214, if it is determined that the value of tempo TMP is not larger than the predetermined maximum value TMPmax, the processing corresponding to step S202 and afterward is performed again. Then, at step S213, music played at the tempo TMP changed by as much as ΔTMP is generated and output again so that the processing corresponding to steps subsequent to step S213 is performed.

Thus, as has been described with reference to FIG. 5, when the values of the heart-rate dispersion caused by the exercise load increased for every fixed time period at the above-described intervals become equivalent to or larger than the predetermined fixed value, the corresponding heart rate can be calculated, as the AT.

In the case where method (a) described with reference to FIGS. 4 and 6 is performed, the AT can be estimated with relative ease by doing an exercise such as jogging while increasing the exercise tempo gradually.

In the case where method (b) described with reference to FIGS. 5 and 7 is performed, the load placed on the user should be controlled with precision by using the bicycle-type training machine, for example. Therefore, the control unit 110 of the reproduction device 100 of the above-described embodiment may be connected to a control unit of the bicycle-type training machine by using a control-signal line or the like so that information about the time where the exercise load is increased and/or decreased, information specifying the exercise load, and so forth are transmitted and/or received between the reproduction device 100 and the bicycle-type training machine. Subsequently, it becomes possible to automatically control the time where the exercise load placed by the bicycle-type training machine is changed and the magnitude of the exercise load.

Of course, by acquiring information about the time where the exercise load is increased and/or decreased from the reproduction device 100, the user may change the exercise load manually, so that the AT is estimated.

In the reproduction device 100 of the above-described embodiment, the AT of the user is estimated by performing method (a) described with reference to FIGS. 4 and 6 so that the AT can be estimated with relative ease.

As described above, the AT estimation is performed at predetermined time intervals, such as once a month, once three months, etc. The estimated AT is stored and held in the nonvolatile memory of the control unit 110, and read and used during the physical-exercise-lead processing. The physical-exercise-lead processing is performed during daily training, for example.

[Details on Physical-Exercise-Lead Processing]

Next, the physical-exercise-lead processing will be described. In the above-described training mode, the body-lead unit 105 and the control unit 110 that are provided in the reproduction device 100 of the above-described embodiment chiefly function in concert with each other, so as to perform the physical-exercise-guide processing in consideration of the AT that had been estimated.

Figure 8:
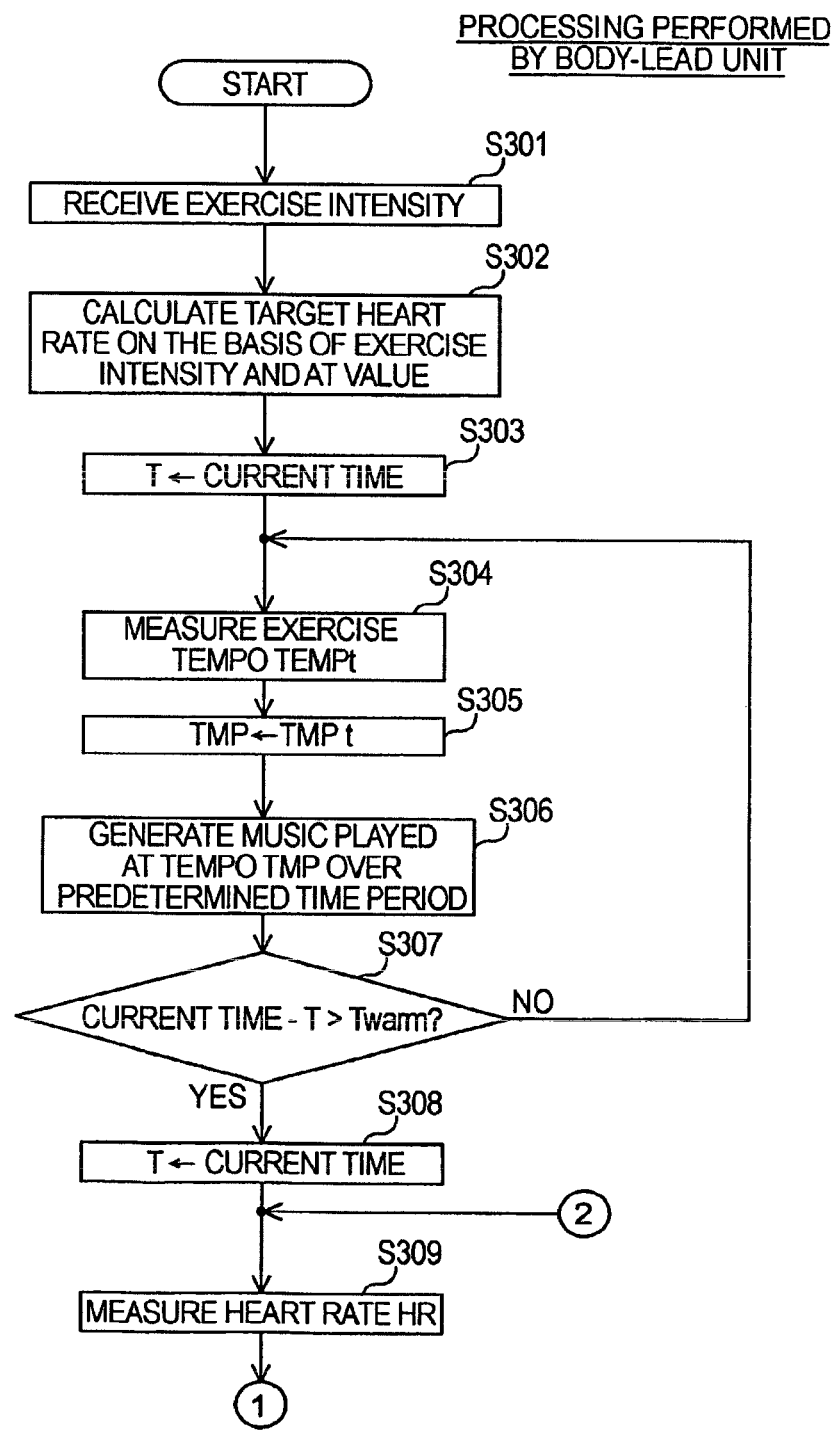
FIG. 8 is a flowchart illustrating physical-exercise-lead processing.
Figure 9:
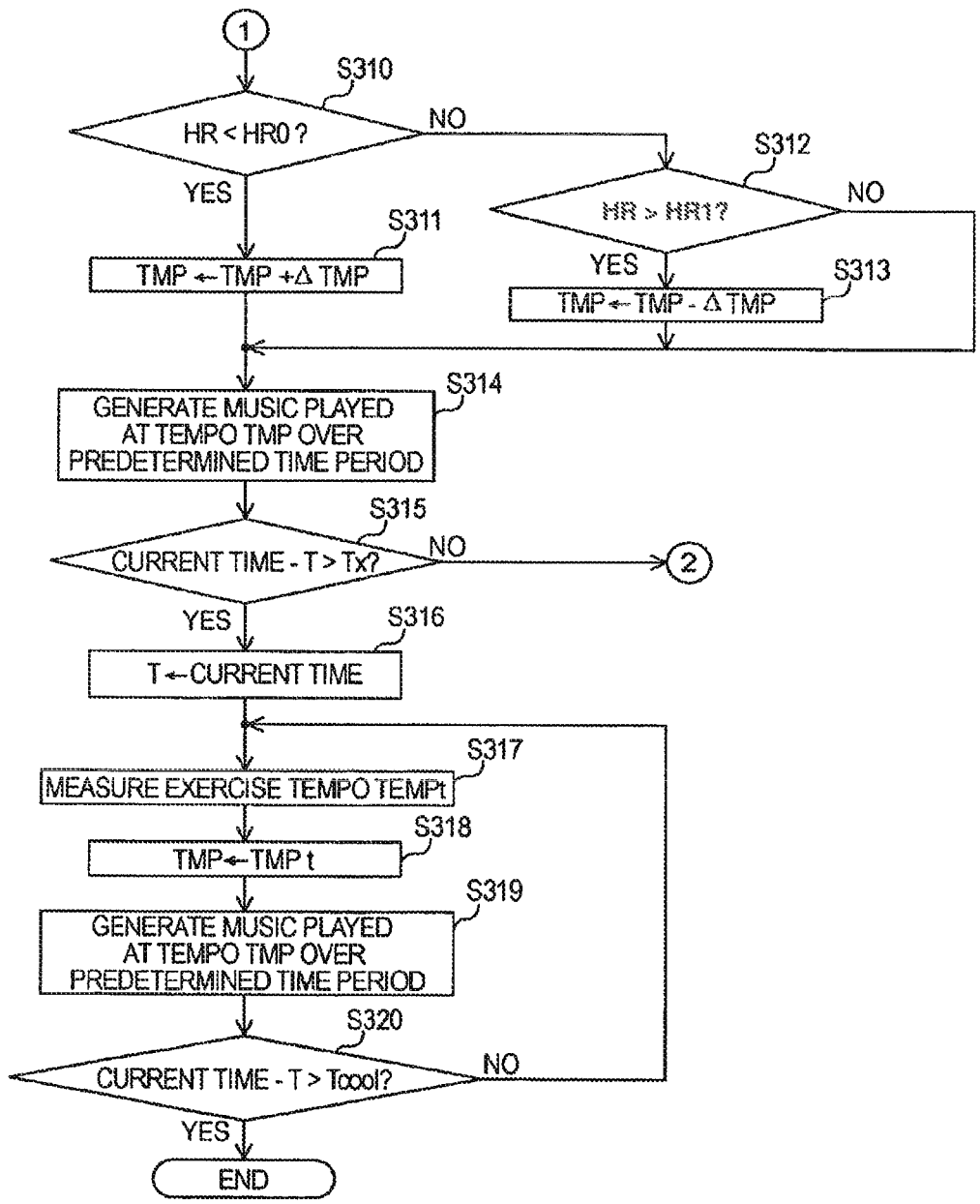
FIG. 9 is a flowchart following the flowchart shown in FIG. 8.

Each of FIGS. 8 and 9 illustrates the physical-exercise-lead processing performed by the reproduction device 100 of the above-described embodiment. Upon receiving a predetermined operation input in the training mode, the control unit 110 performs processing procedures shown in FIGS. 8 and 9.

As described below, in the case where the processing procedures shown in FIGS. 8 and 9 are performed, a warm-up period where a physical exercise is performed over a predetermined time period at the current physical-exercise tempo, the training period where the aerobic exercise is actually performed, and a cooldown period where the physical exercise is performed over another predetermined time period at a physical-exercise tempo appropriate after the training is done are provided.

First, the control unit 110 receives an instruction about the exercise intensity, the instruction being input by the user, via the exercise-intensity-input unit 105 (step S301). The control unit 110 enters waiting mode until the exercise-intensity instruction is input. The exercise-intensity instruction received by the control unit 110 has three levels represented as "slow (light)", "ordinary", and "hard (heavy)", for example. Each of the levels is related to the AT. Namely, predetermined relationships are established between each of the levels and the AT. For example, the level represented as "slow" corresponds to from forty to sixty percent of the AT, the level represented as "ordinary" corresponds to from sixty to eighty percent of the AT, and the level represented as "hard" corresponds to eighty to one hundred percent of the AT.

Then, the control unit 110 transmits the exercise-intensity information received via the exercise-intensity-input unit 104 and the AT that is stored and held in the nonvolatile memory of the control unit 110 and that had already been estimated to the body-guide unit 105, and calculates the range (H0, H1) of the target heart rate (step S302). Thus, in the above-described embodiment, the target heart rate is determined, as the range. In the range (H0, H1), the sign H0 denotes a minimum heart rate and the sign H1 denotes a maximum heart rate.

An example target-heart-rate range will be described below. For example, when the AT that had already been estimated reads 150 pulses per minute, the target-heart-rate range reads (60, 90) when the exercise intensity is on the level "slow", reads (90, 120) when the exercise intensity is on the level "ordinary", and reads (120, 150) when the exercise intensity is on the level "hard".

Then, the control unit 110 acquires the current-time information from the clock circuit thereof, sets the acquired information to the time variable T (step S303), controls the tempo-detection unit 101 so that the current physical-exercise tempo TMPt of the user is measured, and receives information about a result of the measurement (step S304). Further, the control unit 110 assigns the value of the variable TMPt of the current physical-exercise tempo to the variable TMP of the physical-exercise tempo (step S305).

Next, the control unit 110 outputs (reproduces) music played at a tempo represented as the variable TMP over a predetermined time period by controlling the music-generation unit 106 and the music-reproduction unit 108 (step S306). Then, the control unit 110 determines whether or not music played at the current-physical-exercise tempo is output over the time period corresponding to a predetermined warm-up time Twarm (step S307).

Thus, the music played at the tempo of the exercise done by the user is generated and output, as warm-up processing. The warm-up processing corresponds to pacing processing performed, so as to establish rapport, that is, a relationship of trust between a therapist and a client. The term rapport is used in clinical psychology. Subsequent to the warm-up processing, leading processing is performed, so as to lead the user to the target heart rate.

Namely, a warm-up period is provided, so that the user can shift to the training period without difficulty, as is the case with a client led to the leading process by an expert of the clinical psychology, where the expert relaxes the client by adjusting the rhythm of voice and/or establishing eye-to-eye contact with the client so that cautiousness in the client is eliminated and the trust relationship is established between the expert and the client.

If it is determined that the music is not output at the current physical-exercise tempo over the time period corresponding to the warm-up time Twarm, at step S307, the control unit 110 performs the processing corresponding to step S304 and afterward again so that the warm-up processing is continued. If it is determined that the music is output at the current physical-exercise tempo over the time period corresponding to the warm-up time Twarm, at step S307, the control unit 110 determines that the warm-up processing is finished. Subsequently, the control unit 110 acquires the current-time information from the clock circuit thereof and assigns the current-time information to the time variable T (step S308).

Then, the control unit 110 measures the current heart rate HR of the user by controlling the heart-rate-detection unit 102 (step S309). After that, the processing advances to step S310 shown in FIG. 9 so that it is determined whether or not the measured heart rate HR of the user is smaller than the minimum heart rate H0 in the target-heart-rate range (step S310).

If it is determined that the heart rate HR is smaller than the minimum heart rate H0 in the target-heart-rage range, at step S310, the tempo TMP is increased by as much as predetermined ΔTMP (step S311). If it is determined that the heart rate HR is larger than the minimum heart rate H0 in the target-heart-rate range, at step S310, the control unit 110 determines whether or not the measured heart rate HR of the user is larger than the maximum heart rate H1 in the target-heart-rate range (step S312).

If it is determined that the heart rate HR is larger than the maximum heart rate H1 in the target-heart-rate range, at step S312, the tempo TMP is decreased by as much as the predetermined ΔTMP (step S313). After the processing corresponding to step S311, or step S313 is performed, or at step S312, if it is determined that the heart rate HR is smaller than the maximum heart rate H1 in the target-heart-rate range, music played at a tempo indicated by the tempo TMP is generated and output, and presented to the user (step S314).

Then, the control unit 110 acquires the current-time information from the clock circuit thereof and determines whether or not the user did the training over a predetermined training time period Tx (step S315). If it is determined that the training had not done over the predetermined training time period Tx, at S315, the control unit 110 performs the processing corresponding to step S309 and afterward that are shown in FIG. 8 again so that the speed of music reproduction (the output speed) can be controlled. That is to say, the exercise is continued.

If it is determined that the training had done over the predetermined training time period Tx, at step S315, the control unit 110 acquires the current-time information from the clock circuit thereof, sets the acquired current-time information to the time variable T, and measures the tempo TMPt of the currently performed physical exercise by controlling the tempo-detection unit 101 (step S317).

The measured tempo TMPt is set to the variable TMP of the music tempo (step S318) and music played at the tempo TMP is generated over a predetermined time period (step S319). The user does a physical exercise at the above-described music tempo. Then, the control unit 110 acquires the current-time information from the clock circuit and determines whether or not the physical exercise had done over a predetermined cool-down period Tcool (step S320).

If it is determined that the physical exercise had not done over the predetermined cool-down period Tcool, at step S320, the processing corresponding to step S317 and afterward is performed again, and the user does the physical exercise at the current tempo of the physical exercise, so that cooldown is achieved. If it is determined that the physical exercise had done over the predetermined cooldown period, at step S320, the cooldown period is concluded. Therefore, the physical-exercise-lead processing shown in FIGS. 8 and 9 is terminated.

Figure 10:
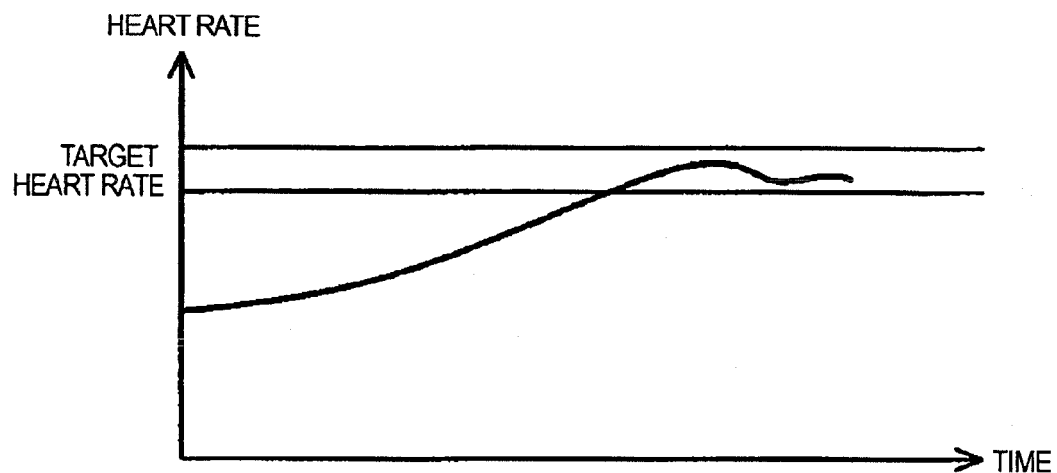
FIG. 10 illustrates an example result of the physical-exercise-lead processing.
Figure 11:
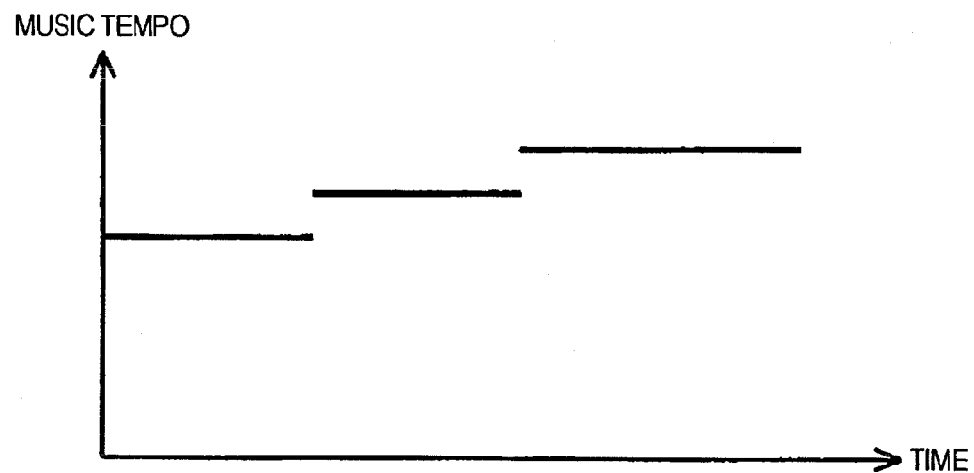
FIG. 11 illustrates another example result of the physical-exercise-lead processing.

FIG. 10 illustrates a change in the heart rate with the passage of time, the change being caused by a change in the music tempo with the passage of time, where the heart-rate change occurs at the time where the user does an exercise while the physical-exercise-lead processing shown in FIGS. 8 and 9 is performed. FIG. 11 illustrates the music-tempo change with the passage of time, the change corresponding to the heart-rate change shown in FIG. 10. As has been described, the tempo of music generated and presented to the user is increased step by step during the exercise period, as shown in FIG. 11.

When the user does an physical exercise including walking, jogging, running, cycling, and so forth at the tempo of reproduced music, the tempo being increased step by step, as described above, an appropriate exercise load is placed on the user's body and the heart rate of the user is increased gradually. Subsequently, the user's heart rate is led into the target heart-rate range (H0, H1), as shown in FIG. 10.

After the user's heart rate enters the target heart-rate range, the cooldown period is provided, so as not to change the physical exercise done by the user to the anaerobic exercise. Subsequently, the user can finish the physical exercise without stress. Therefore, it becomes possible to make the user do only the aerobic exercise with efficiency and stability without placing a significant stress on the user's body.

Thus, the reproduction device 100 of the above-described embodiment can measure the physical state. The physical state denotes motions of the user's body, such as the pulsation of the user. Further, the reproduction device 100 calculates the physical-exercise rhythm (the physical-exercise tempo) and the AT on the basis of the measured physical state, and calculates the physical state suitable for performing a target aerobic exercise on the basis of the AT and input information about the exercise intensity. Further, feedback on body leading performed, so as to attain the calculated physical state, is provided, which makes it possible to support the user so that the user can perform an appropriate aerobic exercise.

[Details on Music Database and Voice Control]

As described above, the music-generation unit 106 generates music played at a target tempo calculated by the body-lead unit 105 by using musical information stored in the music database 107. Data on tracks, meta data on the tracks, and data on musical materials are accumulated on the music database 107.

There are methods (1), (2), and (3) that allow for generating music played at the target tempo. According to method (1), music played at a tempo similar to the target tempo is selected from a database on known music. According to method (2), the tempo of known music is changed into the target tempo. According to method (3), music played at the target is automatically generated.

According to method (1), track data is accumulated on the music database 107. Information about the music tempo is included in data on each track, as meta data. The music database 107 includes a list of track data items sorted in descending order on the basis of the music tempo, as shown in FIG. 12.

FIG. 12 illustrates an example list of the music database. The example list shows information about identifiers (IDs) specifying the track data items, the artist names, the track names, the album names, and track tempos. For generating music played at the target tempo, each of the track tempos shown on the list shown in FIG. 12 may be compared with the target tempo, and a track played at a tempo that is the most similar to the target tempo may be selected and output (reproduced).

According to method (2), the tempo of a reproduced track is adjusted and changed into the target tempo, and the track is output (reproduced). Namely, in the case where the reproduction device 100 of the above-described embodiment is used, the control unit 110 controls the music-reproduction unit 108, so as to change the tempo. Subsequently, it becomes possible to change the tempo of a known track and present the known track played at the changed tempo.

According to method (3), a track is generated by reproducing data MIDI shown on the left side of FIG. 13 according to scores shown on the right side of FIG. 13. Here, rhythm 1 indicates the rhythm of an electric bass guitar and is generated, so that the tempo of the rhythm becomes the same as the tempo of a physical exercise done by the user. For example, when the physical-exercise tempo is quicker and/or slower than the music tempo by as much as ten percent of the music tempo, rhythm 2 is generated so that the tempo thereof becomes the same as the physical-exercise tempo. When the physical-exercise tempo is quicker and/or slower than the music tempo by as much as five percent of the music tempo, rhythm 3 is generated so that the tempo thereof becomes the same as the physical-exercise tempo. Subsequently, a rhythm that is so sophisticated and amusing that the physical-exercise tempo synchronizes with the music tempo is generated and output.

In the above-described embodiment, different tracks with different rhythms such as rhythms (1), (2), and (3) are output according to the tempo of the physical exercise done by the user. However, the present invention can be achieved without being limited to the above-described embodiment. First, a musical material A is output at the same tempo as the tempo of the physical exercise done by the user, for example. Next, when the physical-exercise tempo is quicker and/or slower than the music tempo by as much as ten percent of the music tempo, a musical material B is output in addition to the musical material A, for example. In that case, the musical materials A and B may be merged with each other, or a musical material generated by merging the musical materials A and B with each other may be prepared in advance and output.

When the physical-exercise tempo is quicker and/or slower than the music tempo by as much as five percent of the music tempo, a musical material C is output at the same tempo as the physical-exercise tempo in addition to the musical materials A and B. In that case, the musical materials A, B, and C may be merged with one another. Otherwise, a musical material including the musical materials A, B, and C that are merged with one another may be prepared in advance and output. Subsequently, music that is so sophisticated and amusing that the physical-exercise tempo synchronizes with the music tempo can be generated and output.

The above-described three methods, namely, methods (1), (2), and (3) may be used at the same time. For example, a track played at a music tempo similar to the target tempo may be selected from the music database, the track may be output so that the music tempo thereof is synchronized with the target tempo, and another sound source may further be used so that sound output from the sound source and the output track overlap with each other.

Further, the physical-exercise-lead processing of the reproduction device 100 of the above-described embodiment presents three periods including the warm-up period, the training period, and cooldown period. Therefore, it becomes possible to change tracks used in each of the periods, set the priority of the tracks used in the periods, and determine and set the tracks used in the periods in advance.

Further, the above-described embodiment allows for selecting and outputting a track played at a tempo similar to the target tempo from the music database, or changing the tempo of the selected track into the same tempo as the target tempo. Further, the above-described embodiment allows for leading the tempo of the physical exercise done by the user by generating and outputting a track played at the target tempo so that the user can do a target physical exercise without stress. However, the present invention can be achieved without using music.

For example, a pulse sound or the sound of a percussion instrument may be used. Otherwise, the cycle of vibrations and/or flashing lights transmitted to the user, the cycle of a still image displayed and presented to the user, and the speed of video reproduction may be controlled so that the tempo of the physical exercise done by the user is led. That is to say, in the above-described embodiment, the user may be provided with a rhythm via the senses of hearing, touch, and sight so that the tempo of the physical exercise done by the user is led, as in the case where the tempo of the physical exercise done by the user is led by using music.

Further, according to the above-described embodiment, the present invention is used for the mobile music-reproduction device. However, the present invention can be achieved without being limited to the above-described embodiment. For example, in consideration of the case where the user does training indoors, such as a training gym, by using a running machine and/or a bicycle-type training machine, it is designed that the user wears an acceleration sensor detecting the tempo of the physical exercise done by the user and/or a heart-rate sensor detecting the heart rate of the user. An output of the detection is transmitted to a so-called stationary music-reproduction device over wires and/or wirelessly, and music may be output from the stationary music-reproduction device, so as to lead the tempo of the physical exercise done by the user. That is to say, the present invention can be used for the stationary music-reproduction device, for example.

The present invention can be used for a so-called fitness machine such as a running machine, a bicycle-type training machine, and so forth that include a music-reproduction unit so that the user can do training while listening to music.

Further, in the above-described embodiment, the acceleration sensor is used, so as to detect the physical-exercise rhythm. However, the present invention can be achieved without being limited to the above-described embodiment. Namely, various sensor elements that can detect the physical-exercise rhythm may be used, where the various sensor elements include a pressure sensor and/or a vibration sensor mounted on a shoe worn by the user doing exercises.

Further, according to the above-described embodiment, the reproduction device 100 is mounded onto the hips of the user, for example. However, the present invention can be achieved without being limited the above-described embodiment. Namely, the reproduction device 100 may be changed in shape, size, and so forth so that the reproduction device 100 can be mounted onto the body of the user at a most appropriate position such as the arm, the head, and so forth, in consideration of the usage mode of the user and/or the type of a physical exercise done by the user.

Further, in the above-described embodiment, the AT-estimation unit 103 and the control unit 110 operate in concert with each other, so as to acquire the AT, and the exercise-intensity-input unit 104 receives information about the exercise intensity, and the body-lead unit 105 and the control unit 110 operate in concert with each other, so as to calculate a value indicating the target physical state. Further, body-guide unit 105 and the control unit 110 operate in concert with each other, so as to control a sound output.

Functions of the tempo-detection unit 101 and the heart-rate detection unit 102 other than functions achieved by the acceleration sensor and the heart-rate sensor can be achieved through a program executed by the control unit 110. Functions of the AT-estimation unit 103 and the body-lead unit 105 can be achieved through the program executed by the control unit 110.

Namely, since a program executed by a computer can be installed into a music-reproduction device that has the function of reproducing music and that can receive an instruction input by a user, the present invention can be used for a known music-reproduction device or the like. When the program is executed, steps (1), (2), (3), (4), and (5) are performed in that order, as described below. First, an AT is acquired, at step (1), input information about the exercise intensity is received, at step (2), a value indicating a target physical state is calculated on the basis of the acquired AT and the received exercise-intensity information, at step (3), a value indicating the current physical state of the user is detected, at step (4), and sound reproduction is controlled on the basis of the result of a comparison of the calculated target physical-state value and a value indicating the detected current physical state, so as to lead the physical exercise done by the user so that the physical state of the user attains the target physical state, at step (5).

Of course, the AT acquisition corresponding to step (1) may be achieved by using method (a) described with reference to FIGS. 4 and 6, and/or method (b) described with reference to FIGS. 5 and 7. Further, the sound-reproduction control corresponding to step (5) may be achieved by using the method described with reference to FIGS. 8 and 9. That is to say, when a program that can perform the steps shown in the flowchart shown in FIG. 6 is generated and installed into a sound-output device including a music-reproduction device or the like with a computer mounted therein, and when preparations are made for executing the program, the AT of the user can be acquired. The AT of the user can also be acquired by generating and installing a program that can perform the steps shown in the flowchart shown in FIG. 7 into the above-described sound-output device, and executing the program.

Further, by generating and installing a program that can perform the steps shown in the flowcharts of FIGS. 8 and 9 into a music-reproduction device or the like with a computer mounted therein, and executing the program, a device is achieved, the device being capable of leading the user so that the user can perform a physical exercise, for example, running, jogging, walking, cycling, etc., as an aerobic exercise, with efficiency, stability, and no stress. Namely, the device allows the user to perform the aerobic exercise effectively.

It should be understood by those skilled in the art that various modifications, combinations, sub-combinations and alterations may occur depending on design requirements and other factors insofar as they are within the scope of the appended claims or the equivalents thereof.

What is claimed is:

1. A mobile information processing apparatus comprising:
a processor configured to receive a heart rate of a user from a sensor and output an audio signal,
wherein the processor is configured to change an original tempo of the audio signal to a current tempo based on a comparison between the heart rate and a target heart rate range,
wherein the processor is configured to determine the target heart rate range based on at least an exercise intensity specified by the user and an anaerobic threshold of the user, the target heart rate range thereby being a user-defined target heart rate range,
wherein the mobile information processing apparatus is configured to be worn by the user, and
wherein the processor is configured to change the current tempo of the audio signal according to a change of the comparison to lead the heart rate of the user to the user-defined target heart rate range, wherein the processor is configured to change the current tempo by selecting a track from a database of tracks and associated tempos based on a target tempo, and the processor is configured to output the audio signal to play the selected track, wherein the processor is configured to estimate the anaerobic threshold at least in part by gradually increasing a tempo of the audio signal while the heart rate is detected.

2. The mobile information processing apparatus according to claim 1, wherein the current tempo of the audio signal has been changed so as to be faster than the original tempo of the audio signal if the heart rate is less than the target heart rate range.

3. The mobile information processing apparatus according to claim 1, wherein the current tempo of the audio signal has been changed so as to be slower than the original tempo of the audio signal if the heart rate is greater than the target heart rate range.

4. The mobile information processing apparatus according to claim 1, further comprising an acceleration sensor, wherein the acceleration sensor is configured to measure an exercise rhythm based on a vertical motion of a body of the user and/or a lateral motion of the body of the user.

5. The mobile information processing apparatus according to claim 4, wherein the processor is configured to calculate an exercise tempo indicating a cycle of the exercise rhythm based on the measured exercise rhythm.

6. The mobile information processing apparatus according to claim 1, wherein the sensor is attached to a headphone.

7. The mobile information processing apparatus according to claim 1, wherein the processor receives the audio signal from an external device.

8. The mobile information processing apparatus according to claim 1, further comprising a memory which stores the audio signal.

9. The mobile information processing apparatus according to claim 1, wherein the processor is configured to acquire data related to user motion from a second sensor, and the second sensor is at least one of an acceleration sensor, a pressure sensor or a vibration sensor.

10. The mobile information processing apparatus according to claim 9, wherein the second sensor is attached to a shoe worn by the user.

11. A mobile information processing apparatus comprising:

a processor configured to output an audio signal, wherein the processor is configured to change an original tempo of the audio signal to a current tempo based on a comparison between a heart rate of a user detected by a sensor and a target heart rate range, wherein the processor is configured to determine the target heart rate range based on at least an exercise intensity specified by the user and an anaerobic threshold of the user, the target heart rate range thereby being a user-defined target heart rate range, wherein the anaerobic threshold is determined from a slope or stability of the user's heart rate with a varied exercise load or intensity, and wherein the processor is configured to change the current tempo of the audio signal according to a change of the comparison to lead the heart rate of the user to the user-defined target heart rate range, wherein the processor is configured to change the current tempo by selecting a track from a database of tracks and associated tempos based on a target tempo, and the processor is configured to output the audio signal to play the selected track, wherein the mobile information processing apparatus is configured to be worn on an arm of the user, wherein the processor is configured to estimate the anaerobic threshold at least in part by gradually increasing varying a tempo of the audio signal while the heart rate is detected.

12. The mobile information processing apparatus according to claim 11, wherein the current tempo of the audio signal has been changed so as to be faster than the original tempo of the audio signal if the heart rate is less than the target heart rate range.

13. The mobile information processing apparatus according to claim 11, wherein the current tempo of the audio signal has been changed so as to be slower than the original tempo of the audio signal if the heart rate is greater than the target heart rate range.

14. The mobile information processing apparatus according to claim 11, further comprising an acceleration sensor, wherein the acceleration sensor is configured to measure an exercise rhythm based on a vertical motion of a body of the user and/ or a lateral motion of the body of the user.

15. The mobile information processing apparatus according to claim 14, wherein the processor is configured to calculate an exercise tempo indicating a cycle of the exercise rhythm based on the measured exercise rhythm.

16. The mobile information processing apparatus according to claim 11, wherein the sensor is attached to a headphone.

17. The mobile information processing apparatus according to claim 11, wherein the processor receives the audio signal from an external device.

18. The mobile information processing apparatus according to claim 11, further comprising a memory which stores the audio signal.

19. The mobile information processing apparatus according to claim 11, wherein the processor is configured to acquire data related to user motion from a second sensor, and the second sensor is at least one of an acceleration sensor, a pressure sensor or a vibration sensor.

20. The mobile information processing apparatus according to claim 19, wherein the second sensor is attached to a shoe worn by the user.

21. A mobile information processing apparatus comprising:

a processor configured to receive a heart rate of a user from a sensor and output an audio signal, wherein the audio signal has been selected based on a comparison between the heart rate and a target heart rate range, the processor is configured to determine the target heart rate range based on at least an exercise intensity specified by the user, the target heart rate range thereby being a user-defined target heart rate range, the mobile information processing apparatus is configured to be worn by the user, wherein the processor is configured to change a current tempo of the audio signal according to a change of the comparison to lead the heart rate of the user to the user-defined target heart rate range, wherein the processor is configured to change the current tempo by selecting a track from a database of tracks and associated tempos based on a target tempo, and the processor is configured to output the audio signal to play the selected track, wherein the processor is configured to estimate an anaerobic threshold at least in part by gradually increasing a tempo of the audio signal while the heart rate is detected.

22. The mobile information processing apparatus according to claim 21, wherein the processor is configured to select, as the audio signal, a first audio signal having a tempo faster than a tempo of a second audio signal corresponding to a currently reproduced audio if the heart rate is less than the target heart rate range.

23. The mobile information processing apparatus according to claim 21, wherein the processor is configured to select, as the audio signal, a first audio signal having a tempo slower than a tempo of a second audio signal corresponding to a currently reproduced audio if the heart rate is greater than the target heart rate range.

24. The mobile information processing apparatus according to claim 21, further comprising an acceleration sensor, wherein the acceleration sensor is configured to measure an exercise rhythm based on a vertical motion of a body of the user and/or a lateral motion of the body of the user.

25. The mobile information processing apparatus according to claim 24, wherein the processor is configured to calculate an exercise tempo indicating a cycle of the exercise rhythm based on the measured exercise rhythm.

26. The mobile information processing apparatus according to claim 21, wherein the sensor is attached to a headphone.

27. The mobile information processing apparatus according to claim 21, wherein the processor receives the audio signal from an external device.

28. The mobile information processing apparatus according to claim 21, further comprising a memory which stores the audio signal.

29. The mobile information processing apparatus according to claim 21, wherein the processor is configured to acquire data related to user motion from a second sensor, and the second sensor is at least one of an acceleration sensor, a pressure sensor or a vibration sensor.

30. The mobile information processing apparatus according to claim 29, wherein the second sensor is attached to a shoe worn by the user.

31. A non-transitory computer-readable medium storing instructions which, when executed by a processor of a mobile information processing apparatus, perform a method comprising:

receiving a heart rate of a user from a sensor;

outputting an audio signal; and changing an original tempo of the audio signal to a current tempo based on a comparison between the heart rate and a target heart rate range, wherein the target heart rate range is determined based on at least an exercise intensity specified by the user and an anaerobic threshold of the user, the target heart rate range thereby being a user-defined target heart rate range, wherein the mobile information processing apparatus is configured to be worn by the user, and wherein the processor is changes the current tempo of the audio signal according to a change of the comparison to lead the heart rate of the user to the user-defined target heart rate range, wherein the processor changes the current tempo by selecting a track from a database of tracks and associated tempos based on a target tempo, and the processor outputs the audio signal to play the selected track, and wherein the processor is configured to estimate the anaerobic threshold at least in part by gradually increasing a tempo of the audio signal while the heart rate is detected.

32. A non-transitory computer-readable medium storing instructions which, when executed by a processor of a mobile information processing apparatus, perform a method comprising:

receiving a heart rate of a user from a sensor; and outputting an audio signal selected based on a comparison between the heart rate and a target heart rate range, wherein the target heart rate range is determined based on at least an exercise intensity specified by the user and an anaerobic threshold of the user, the target heart rate range thereby being a user-defined target heart rate range, wherein the anaerobic threshold is determined from a slope or stability of the user's heart rate with a varied exercise load or intensity, and changes a current tempo of the audio signal according to a change of the comparison to lead the heart rate of the user to the user-defined target heart rate range, wherein the processor changes the current tempo by selecting a track from a database of tracks and associated tempos based on a target tempo, and the processor outputs the audio signal to play the selected track, wherein the mobile information processing apparatus is configured to be worn on an arm of the user, wherein the processor is configured to estimate the anaerobic threshold at least in part by gradually increasing varying a tempo of the audio signal while the heart rate is detected.

* * * * *